United States Patent [19]

Enders et al.

[11] 4,101,575
[45] Jul. 18, 1978

[54] N-ARYL-N'-(2,3-DIHALOGENO-ALKANOYL)-UREAS

[75] Inventors: Edgar Enders, Cologne; Helmut Kaspers, Leverkusen; Wilhelm Brandes, Cologne, all of Germany

[73] Assignee: Bayer Aktiengesellschaft, Leverkusen, Germany

[21] Appl. No.: 668,165

[22] Filed: Mar. 18, 1976

[30] Foreign Application Priority Data

Mar. 20, 1975 [DE] Fed. Rep. of Germany ....... 2512171

[51] Int. Cl.² ...................... C07C 127/22; A01N 9/20
[52] U.S. Cl. ............................ 260/553 E; 260/302 R; 260/307 D; 260/378; 260/463; 260/465 D; 424/270; 424/272; 424/273 R; 424/301; 424/304; 424/322; 548/306
[58] Field of Search ...................... 424/322; 260/553 E

[56] References Cited
U.S. PATENT DOCUMENTS

| 2,801,200 | 7/1957 | Hackmann | 260/553 E X |
| 3,551,159 | 12/1970 | Froehlich | 260/553 E X |
| 3,627,778 | 12/1971 | Nusslein et al. | 260/553 E X |
| 4,036,850 | 7/1977 | Enders | 260/553 E X |

FOREIGN PATENT DOCUMENTS 12,152R  2/1970  Japan .................... 424/322

OTHER PUBLICATIONS

Taber et al., CA 71:51505s (1969).

*Primary Examiner*—Daniel E. Wyman
*Assistant Examiner*—Thomas A. Waltz
*Attorney, Agent, or Firm*—Burgess, Dinklage & Sprung

[57] ABSTRACT

N-Aryl- or -heteroaryl-N'-(2,3-dihalogeno-alkanoyl)-ureas of the formula

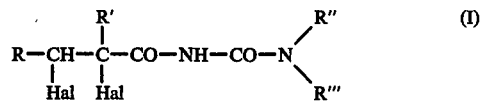

in which
  R and R' each independently is hydrogen or alkyl,
  R" is optionally substituted aryl or heteroaryl,
  R''' is hydrogen, optionally substituted alkyl, cycloalkyl or benzyl, or aryl, and
  Hal is chlorine or bromine
which possess fungicidal and bactericidal properties.

7 Claims, No Drawings

N-ARYL-N'-(2,3-DIHALOGENO-ALKANOYL)-UREAS

The present invention relates to and has for its objects the provision of particular new N-aryl- or -heteroaryl-N'-(2,3-dihalogeno-alkanoyl)-ureas which possess fungicidal and bactericidal properties, active compositions in the form of mixtures of such compounds with solid and liquid dispersible carrier vehicles, and methods for producing such compounds and for using such compounds in a new way especially for combating pests, e.g. fungi and bacteria, with other and further objects becoming apparent from a study of the within specification and accompanying examples.

It is known from "Chemie der Pflanzenschutz- and Schädlingsbekämpfungsmittel" ("Chemistry of Plant Protection Agents and Pesticides"), Volume 2, pages 65 and 108, published by R. Wegler, Springer-Verlag Berlin/Heidelberg/New York (1970), that zinc ethylene-1,2-bis-dithiocarbamate (Compound A) or N-trichloromethylthio-tetrahydrophthalimide (Compound B) can be used as a fungicidal agent against phytopathogenic fungi. These compounds have found worldwide acceptance as commercially available products in plant protection and can be described as standard preparations. However, the action of these compounds is not always satisfactory, especially if low amounts are used.

The present invention provides, as new compounds, the 2,3-dihalogen-alkanoyl-ureas of the general formula

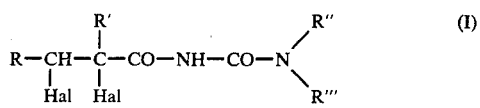

in which
R and R' each independently is hydrogen or alkyl,
R" is optionally substituted aryl or heteroaryl,
R''' is hydrogen, optionally substituted alkyl, cycloalkyl or benzyl, or aryl, and
Hal is chlorine or bromine.

The compounds of the formula (I) have been found to exhibit strong fungicidal properties.

Preferably R and R' are each hydrogen or alkyl with up to 5 carbon atoms and R'''is hydrogen, alkyl with 1 to 6 carbon atoms (which is optionally substituted by cyano, methoxy, ethoxy, methylthio or ethylthio), cyclohexyl, benzyl or phenyl (phenyl being especially preferred). R" is preferably a phenyl, naphthyl, anthracenyl, anthraquinolyl, benzthiazolyl, benzoxazolyl or benzimidazolyl radical, which aromatic and heteroaromatic radicals can be monosubstituted or poly-substituted, preferably as halogen, hydroxyl, nitro, cyano, alkyl with 1 to 12 carbon atoms, alkoxy or alkylthio, each with 1 to 6, especially 1 to 4, carbon atoms, halogenoalkyl or halogenoalkylthio, each with 1 or 2 carbon atoms and 1 to 5 halogen atoms (especially fluorine and/or chlorine), or by phenyl, phenoxy or phenylthio, the three last-mentioned radicals themselves being optionally substituted by halogen and/or nitro. Further preferred substituents are phenylamino, alkylamino and dialkylamino groups wherein the alkyl groups contain 1 to 4, especially 1 or 2, carbon atoms, a heterocyclic ring including a linking hetero nitrogen atom wherein the heterocyclic ring can also contain nitrogen, oxygen or sulfur atoms as further hetero-atoms; pyrrolidino, 2-oxo-pyrrolidino, imidazolidino, morpholino and maleimido radicals may be mentioned as examples of such ring systems. Further possible substituents of the aromatic or hetero-aromatic radicals R" are acetyl, aldehyde, thiocyanate, benzyl and benzoyl groups (the two last-mentioned groups optionally being chlorine-substituted), phenylsulfinyl, phenylsulfonyl, alkylsulfinyl and alkylsulfonyl groups (the four last-mentioned radicals optionally containing chlorine or fluorine as further substituents), cycloalkyl and cycloalkenyl groups, each with 5 or 6 carbon atoms, alkenyloxy groups with 2 to 4 carbon atoms (as examples of which the allyloxy and methallyloxy group may be mentioned), optionally chlorine-substituted acylamino groups with 1 to 6, especially 2 to 4, carbon atoms, alkylsulfonyloxy groups with 1 to 6 carbon atoms and arylsulfonyloxy groups (the methane-sulfonyloxy and phenylsulfonyloxy group being mentioned as examples of the two last-mentioned radicals), alkylamidosulfonyl groups and dialkylamidosulfonyl groups with 1 to 6 carbon atoms in each alkyl group, the two alkyl radicals optionally forming, together with the amine nitrogen atom, a heterocyclic ring (the dimethylamidosulfonyl, ethylamidosulfonyl and butylamidosulfonyl being mentioned as examples) and a heterocyclicamidosulfonyl group linked through a hetero nitrogen atom such as piperidinosulfonyl. Yet further substituents are arylamidosulfonyl groups which may be optionally chlorine-substituted (for example, the chlorophenylamidosulfonyl group), alkylamidocarbonyl and dialkylamidocarbonyl groups wherein the alkyl radicals contain 1 to 4, especially 1 or 2, carbon atoms (methylamidocarbonyl and dimethylamidocarbonyl groups being mentioned as examples) and a heterocyclicamidocarbonyl group linked through a hetero nitrogen atom wherein the heterocyclic ring can contain further hetero atoms, such as oxygen e.g. morpholinocarbonyl.

Furthermore, R" can also preferentially be a group of the general formula

wherein
X is a radical of the general formula

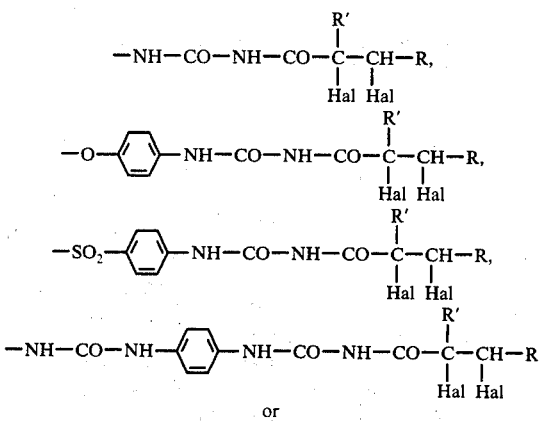

or

-continued

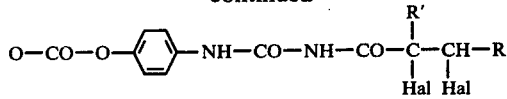

wherein R, R' and Hal have the above-mentioned meanings.

surprisingly, the 2,3-dihalogen-alkanoyl-ureas according to the invention exhibit a substantially greater fungicidal action than the above-mentioned known commercially available products. The compounds according to the invention thus represent an enrichment of the art.

The present invention also provides a process for the preparation of a 2,3-dihalogen-alkanoyl-urea of the formula (I), in which a 2,3-dihalogeno-alkanoyl-isocyanate of the general formula

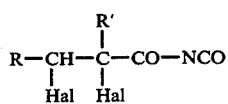 (II), in which
R, R' and Hal have the above-mentioned meanings, is reacted with a primary or secondary amine of the general formula

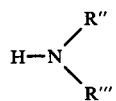 (III), in which
R'' and R''' have the above-mentioned meanings, in the presence of an inert diluent or solvent.

If 2,3-dibromo-propionyl-isocyanate and aniline are used as starting materials, the course of the reaction can be represented by the following equation:

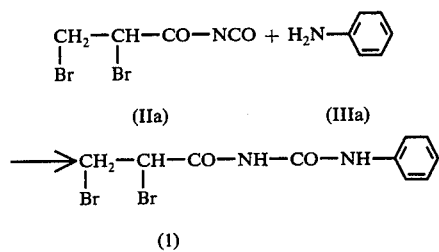

The compounds of the formula (II) have not previously been described in the literature. They can be prepared by adding chlorine or bromine to corresponding alkenecarboxylic acid amides, such as, for example, acrylamide, preferably in inert solvents, for example halogenohydrocarbons, and preferably in the temperature range between −10° and +30° C, and reacting the resulting adduct, if appropriate without intermediate isolation thereof, with oxalyl chloride, the latter reaction preferably being carried out at between +50° and 100° C. This results in the formation of the desired starting products of the formula (II), with elimination of hydrogen halide and carbon monoxide (see also the data in the preparative Examples hereinafter). The following may be mentioned as examples of compounds of the formula (II): 2,3-dibromopropionyl isocyanate, 2,3-dichloro-propionyl isocyanate, 2,3-dibromo-2-methyl-propionyl isocyanate, 2,3-dichloro-2-methyl-propionyl isocyanate, 2,3-dibromo-butyryl isocyanate, 2,3-dichloro-butyryl isocyanate, 2,3-dichloro-2-methyl-butyryl isocyanate, 2,3-dibromo-n-pentanoyl isocyanate and 2,3-dichloro-n-octanoyl isocyanate.

Examples of the amines of the formula (III) are: aniline, 2-, 3- or 4-chloroaniline, 3,4-dichloro-aniline, 2,4-dichloro-aniline, 2,6-dichloroaniline, 3,5-dichloroaniline, 2,4,5-, 2,4,6- and 3,4,5-trichloroaniline, 4-bromoaniline, 2-chloro-4-bromoaniline, 2-methyl-4-chloroaniline, 4-iodoaniline, 4-fluoroaniline, 2-, 3- and 4-methylaniline, 2,4,5-trimethylaniline, 4-tert.-butyl-aniline, 4-isohexylaniline, 4-dodecylaniline, 2-ethyl-4-chloro-aniline, 2-isopropyl-4-bromo-aniline, 2,4-dibromo-aniline, 2-methyl-4,5-dichloroaniline, 2,4-, 3,4- and 2,6-dimethyl-aniline, 2,6-diethylaniline, 2,6-diisopropyl-aniline, 4-methyl-2,6-diisopropylaniline, 4-cyclohexenylaniline, 2-, 3- or 4-nitro-aniline, 2-chloro-4-nitro-aniline, 2-chloro-4-nitro-aniline, 3,5-dichloro-4-methoxy-aniline,3,5-dibromo-4-ethylthioaniline, 3,5-dimethyl-4-chloro-aniline, 3,4-dimethoxy-aniline, 2-chloro-5-dimethylamidosulfonyl-aniline, 2-chloro-5-cyanoaniline, 3,5-bis-trifluoromethyl-aniline, 3-methyl-4-allyloxyaniline, 2-chloro-5-dimethylamidocarbonyl-aniline, 3-methyl-4-methoxycarbonylamino-aniline, 2-chloro-4-methanesulfonyloxyaniline, 4-amino-diphenyl, 1-chloro-2-amino-naphthalene, 4-amino-diphenyl ether, 4',2,6-trichloro-4-amino-diphenyl ether, N-methyl-aniline, N-ethyl-aniline, N-isopropyl-aniline, N-cyclohexyl-aniline, N-benzyl-aniline, diphenylamine, N-(2-cyano-ethyl)-aniline, N-(2-methoxy-ethyl)-aniline, N-(2-ethoxycarbonyl-ethyl)-aniline, N-(2-ethylmercapto-ethyl)aniline, N-methyl-4-toluidine, N-ethyl-3-toluidine, N-methyl-4-chloro-aniline, N-methyl-2,4-dichloro-aniline, N-methyl-3,4-dichloro-aniline, N-methyl-4-chloro-2-methyl-aniline, N,2,4-trimethyl-aniline, N,2,6-trimethylaniline, N-methyl-2,6-diisopropyl-aniline, 4-chloro-diphenylamine, N-methyl-1-amino-naphthalene, N-phenyl-1-amino-naphthalene, N-phenyl-2-amino-naphthalene, N-methyl-1-amino-anthracene, N-methyl-1-amino-anthraquinone, N-methyl-4-nitro-aniline, N-methyl-2-chloro-4-nitro-aniline, N-ethyl-2-nitro-4-chloromethylsul-fonyl-aniline, 4',2-dichloro-4-amino-diphenyl sulfide, 4'-dimethylaminosulfonyl -2,6-dichloro-diphenyl ether, 4',2-dichloro-4-amino-diphenyl sulfoxide, 4',2-dichloro-4-aminodiphenylsulfone, 4',2,6-trichloro-4-amino-diphenylsulfone, 4'-chloro-4-amino-benzophenone, 4'-chloro-4-amino-diphenylmethane, 1-, 2- and 9-aminoanthracene, 1- and 2-aminoanthraquinone, 1,4-diamino-benzene, 1,3-diamino-benzene, 4,4'-diamino-diphenyl ether, 4,4'-diamino-diphenylsulfone, 4,4'-diaminodiphenylurea and 4,4'-diamino-diphenyl carbonate.

The amines listed are compounds generally known to those skilled in the art, and which can be prepared according to methods which are generally known and customary in the laboratory.

Diluents which can be used for the reaction of the compounds of the formula (II) with the compounds of the formula (III) are those organic solvents which are inert towards acyl isocyanates, especially hydrocarbons, for example petroleum ether, ligroin and benzine in the boiling range between 40° and 150° C, benzene, toluene and chlorobenzene; chlorinated alkanes, such as dichloromethane, trichloromethane, carbon tetrachloride or 1,2-dichloroethane; ethers, such as diethyl ether;

ketones, such as acetone; acetonitrile and dimethylformamide.

The reaction temperatures can be varied within a fairly wide range. In general, the reaction is carried out at between −20° and +100° C, preferably between −10° and +50° C.

In carrying out the process according to the invention, preferably 1.0 to 1.1 moles of acyl isocyanate of the formula (II) are employed per mole of the amine according to the formula (III), but it is possible to use amounts which are less or greater than this by up to 20% without significant worsening of the yield. Further details relating to the reaction are to be found in the preparative Examples; working up takes place in a simple manner, by separating off the reaction product which, if the solvent is chosen suitably, crystallizes out from the latter and is in most cases analytically pure. If this is not the case, isolation and purification can be effected by suitable measures, such as concentrating the solution and recrystallizing the residue. In all cases it is necessary to ensure that moisture and solvents containing hydroxyl groups are absent from the reaction mixture, to avoid side-reactions with the acyl isocyanate radical.

The reaction can be carried out, for example, by slowly adding a solution of the 2,3-dihalogeno-alkanoyl isocyanate (II) dropwise to a solution of the amine (III), while stirring and cooling. The concentration of the 2,3-dihalogeno-alkanoyl isocyanate in the solvent is between 5 and 100% by weight, preferably between 10 and 80% by weight, and the concentration of the amine is between 3 and 60% by weight, preferably between 5 and 40% by weight.

The reaction takes place slightly exothermically and is, if necessary, completed by warming to 30° C - 50° C. The N-aryl-N'-(2,3-dihalogen-acyl)-ureas produced are sparingly soluble in the stated solvents and can be filtered off.

In another embodiment of the process according to the invention, a solution of the 2,3-dihalogeno-alkanoyl isocyanate is first taken and a solution of the amine is slowly added thereto, the reaction conditions otherwise being the same.

The active compounds according to the invention exhibit a strong fungitoxic action. Their low toxicity to warmblooded animals and their good toleration by higher plants permits their use as plant protection agents against fungal diseases. They do not damage crop plants in the concentrations required to combat the fungi. Fungitoxic agents are employed in plant protection for combating fungi from the most diverse classes of fungi, such as Archimycetes, Phycomycetes, Ascomycetes, Basidiomycetes and Fungi Imperfecti.

The active compounds according to the invention can be used against parasitic fungi on above-ground parts of plants, fungi which cause tracheomycosis and attack the plant through the soil, seed-borne fungi and fungi which inhabit the soil. They are particularly active against Phycomycetes, Ascomycetes and Basidiomycetes. The following may be mentioned as important fungi to be combated with the active compounds according to the invention: *Phytophthora infestans, Fusicladium dendriticum* and *Puccinia recondita*.

The active compounds according to the instant invention can be utilized, if desired, in the form of the usual formulations or compositions with conventional inert (i.e. plant compatible or herbicidally inert) pesticide diluents or extenders, i.e. diluents, carriers, or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as Freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other fungicides and bactericides or insecticides, acaricides, nematocides rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1-95% by weight, and preferably 0.5-90% by weight, of the mixture, whereas carrier composition mixtures suitable for direct application or field application generally contemplate those in which the active compound is present in an amount substantially between about 0.0001-2%, preferably 0.005-0.05% by weight of the mixture. Thus, the present invention contemplates overall compositions which comprise mixtures of a conventional dispersible carrier vehicle such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001-95%, and preferably 0.0005-95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50-100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 80% by weight of the active compound or even the 100% active substance alone, e.g. about 20-100% by weight of the active compound.

Furthermore, the present invention contemplates methods of selectively killing, combating or controlling pests, e.g. fungi and bacteria, and more particularly methods of combating fungi, which comprises applying to at least one of correspondingly (a) such fungi, (b) such bacteria, and (c) the corresponding habitat thereof, i.e. the locus to be protected, e.g. to a growing crop, to an area where a crop is to be grown or to a domestic animal, a correspondingly combative or toxic amount, i.e. a fungicidally or bactericidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

Mycelium growth test
Nutrient medium used:
20 parts by weight of agar-agar
200 parts by weight of potato decoction
5 parts by weight of malt
15 parts by weight of dextrose
5 parts by weight of peptone
2 parts by weight of disodium hydrogen phosphate
0.3 part by weight of calcium nitrate
Composition of the solvent mixture:
0.19 part by weight of acetone
0.01 part by weight of emulsifier (alkylaryl polyglycol ether)
1.80 parts by weight of water
Ratio of solvent mixture to nutrient medium:
2 parts by weight of solvent mixture
100 parts by weight of agar nutrient medium The amount of active compound required for the desired active compound concentration in the nutrient medium was mixed with the stated amount of solvent. The concentrate was thoroughly mixed, in the stated proportion, with the liquid nutrient medium (which had been cooled to 42° C) and was then poured into Petri dishes of 9 cm diameter. Control plates to which the preparation had not been added were also set up.

When the nutrient medium had cooled and solidified, the plates were inoculated with the species of fungi stated in the table and incubated at about 21° C.

Evaluation is carried out after 4-10 days, dependent upon the speed of growth of the fungi. When evaluation was carried out the radial growth of the mycelium on the treated nutrient media was compared with the growth on the control nutrient medium. In the evaluation of the fungus growth, the following characteristic values were used:

1 no fungus growth
up to 3 very strong inhibition of growth
up to 5 medium inhibition of growth
up to 7 slight inhibition of growth
9 growth equal to that of untreated control.

The active compounds, the active compound concentrations and the results can be seen from the following table:

Table 1

| Active compound | Active compound concentration ppm | Mycelium growth test — Fungi and 1 bacterium | | | | | | | | | | | | | |
|---|---|---|---|---|---|---|---|---|---|---|---|---|---|---|---|
| | | Fusarium culmorum | Sclerotinia sclerotiorum | Fusarium nivale | Colletotrichum coffeanum | Rhizoctonia solani | Pythium ultimum | Cochliobolus miyabeanus | Botrytis cinerea | Verticillium alboatrum | Pyricularia oryzae | Helminthosporium gramineum | Mycosphaerella musicola | Phytophthora cactorum | Pellicularia sasakii |
| (known) CH$_2$—NH—CS—S / CH$_2$—NH—CS—S  Zn  (A) | 10 / 25 | 9/5 | 9/9 | 9/5 | 9/9 | 9/5 | 5/1 | 9/5 | 9/9 | 9/9 | 5/1 | 9/5 | 9/2 | 9/5 | 5/1 |
| [Structure (6): 3,5-diCl-C$_6$H$_3$—NH—C(O)—NH—C(O)—CBr$_2$—CH$_2$Br] | 10 | 5 | 1 | 5 | 3 | 1 | 1 | 5 | 5 | — | 2 | 2 | 1 | 5 | 1 |
| [Structure (2): 3,4-diCl-C$_6$H$_3$—NH—C(O)—NH—C(O)—CCl$_2$—CH$_2$Cl] | 10 | 3 | 3 | 1 | 1 | 1 | 1 | 3 | 5 | 5 | 2 | 1 | 1 | 1 | 1 |
| [Structure (29): (C$_6$H$_5$)$_2$N—C(O)—NH—C(O)—CCl$_2$—CH$_2$Cl] | 10 | — | — | — | 2 | 1 | 1 | 5 | — | — | 1 | 1 | 5 | 3 | 3 |
| [Structure (36): 3,4-diCl-4-CH$_3$-C$_6$H$_3$—NH—C(O)—NH—C(O)—CCl$_2$—CH$_2$Cl] | 10 | 1 | 1 | 1 | 1 | 1 | — | 3 | — | 5 | 1 | 1 | 1 | 3 | 1 |
| [Structure (37): 3-CH$_3$-4-Cl-C$_6$H$_3$—NH—C(O)—NH—C(O)—CCl$_2$—CH$_2$Cl] | 10 | 1 | 1 | 1 | 1 | 1 | 1 | 2 | 5 | — | 3 | 5 | 3 | 1 | 1 |
| [Structure (20): N-CH$_3$ derivative; CBr$_2$—CH$_2$Br] | 10 | — | 3 | — | 2 | 1 | — | — | — | — | 1 | 3 | — | 2 | 3 |
| [Structure (26): N-CH$_3$ derivative; CCl$_2$—CH$_2$Cl] | 10 | — | — | — | 3 | 1 | 1 | 5 | — | — | 1 | 1 | 5 | 1 | 1 |
| [Structure (26): 2,5-diCl-N-CH$_3$ derivative; CCl$_2$—CH$_2$Cl] | 10 | — | 5 | — | 1 | 1 | 1 | 5 | — | — | 1 | 1 | 5 | 1 | 1 |

Table 1-continued

| Active compound | Active compound concentration ppm | Fusarium culmorum | Sclerotinia sclerotiorum | Fusarium nivale | Colletotrichum coffeanum | Rhizoctonia solani | Pythium ultimum | Cochliobolus miyabeanus | Botrytis cinerea | Verticillium alboatrum | Pyricularia oryzae | Helminthosporium gramineum | Mycosphaerella musicola | Phytophthora cactorum | Pellicularia sasakii |
|---|---|---|---|---|---|---|---|---|---|---|---|---|---|---|---|
| (2,4-Cl₂-C₆H₃)N(CH₃)–CO–NH–CO–CBr₂–CH₂Br (5) | 10 | — | — | — | — | 1 | 2 | — | — | — | 1 | 1 | — | 1 | 1 |
| (3-Br,4-Br-C₆H₃)NH–CO–NH–CO–CBr₂–CH₂Br (23) | 10 | 1 | 5 | 5 | 1 | 1 | 2 | — | — | 5 | 1 | 1 | 1 | 1 | 1 |
| (3-Br,4-Cl-C₆H₃)NH–CO–NH–CO–CCl₂–CH₂Cl (33) | 10 | 1 | 1 | 5 | 1 | 1 | 2 | — | — | 5 | 1 | 1 | 1 | 1 | 1 |
| (2-CH₃,4-Cl-C₆H₃)N(CH₃)–CO–NH–CO–CBr₂–CH₂Br (21) | 10 | — | 5 | — | 1 | 1 | 2 | — | — | — | 1 | 1 | 1 | 1 | 1 |
| (C₆H₅)NH–CO–NH–CO–CBr₂–CH₂Br (1) | 10 | 1 | 3 | 1 | 1 | 1 | 1 | 1 | 5 | 3 | 1 | 1 | 2 | 1 | 1 |
| (4-Cl-C₆H₄)NH–CO–NH–CO–CCl₂–CH₂Cl (9) | 10 | 1 | 1 | 1 | 1 | 1 | 1 | 5 | 1 | 1 | 1 | 1 | 1 | 1 | 1 |
| (2-CH₃,4-Cl-C₆H₃)NH–CO–NH–CO–CCl₂–CH₂Cl (34) | 10 | 1 | 1 | 1 | 1 | 1 | 1 | 1 | — | 5 | 1 | 1 | 1 | 1 | 1 |
| (2-Cl,4-CH₃-C₆H₃)NH–CO–NH–CO–CCl₂–CH₂Cl (35) | 10 | 1 | 1 | 1 | 1 | 1 | 3 | 5 | — | — | 1 | 1 | 3 | 1 | 1 |
| (2-Cl,4-Cl-C₆H₃)NH–CO–NH–CO–CCl₂–CH₂Cl (18) | 10 | — | 1 | 1 | 1 | 1 | 1 | — | — | 5 | 1 | 1 | 2 | 1 | 1 |
| (2-Cl,3-Cl-C₆H₃)NH–CO–NH–CO–CCl₂–CH₂Cl (31) | 10 | 1 | 1 | 1 | 1 | 1 | 1 | — | — | — | 1 | 1 | — | 1 | 1 |

EXAMPLE 2

Fusicladium test (apple)/(protective)
Solvent: 4.7 parts by weight of acetone
Emulsifier: 0.3 part by weight of alkylaryl polyglycol ether
Water: 95.0 parts by weight The amount of active compound required for the desired concentration of the active compound in the spray liquid was mixed with the stated amount of solvent, and the concentrate was diluted with the stated amount of water which contained the stated additions.

Young apple seedlings in the 4 – 6 leaf stage were sprayed with the spray liquid until dripping wet. The plants remained in a greenhouse for 24 hours at 20° C and at a relative atmospheric humidity of 70%. They were then inoculated with an aqueous conidium suspension of the apple scab causative organism (Fusicladium dendriticum) and incubated for 18 hours in a humidity chamber at 18°-20° C and at a relative atmospheric humidity of 100%.

The plants were then brought into a greenhouse for 14 days.

15 days after inoculation, the infection of the seedlings were determined. The assessment data were converted to percent infection. 0% means no infection; 100% means that the plants were totally infected.

The active compounds, the concentrations of the active compounds and the results can be seen from the following table:

Table 2

Fusicladium test (apple)/protective

| Active compound | Infection in % at an active compound concentration of | |
|---|---|---|
| | 0.01% | 0.0025% |
| (known) (B) — cyclohexene dicarboximide N—S—CCl₃ | 7 | 24 |
| (18) — 2,3-dichlorophenyl-NH-CO-NH-CO-CHCl-CH₂Cl | 2 | 2 |
| (30) — 2,5-dichlorophenyl-NH-CO-NH-CO-CHCl-CH₂Cl | 1 | 9 |
| (31) — 2,3,6-trichlorophenyl-NH-CO-NH-CO-CHCl-CH₂Cl | — | 5 |
| (6) — 3,5-dichlorophenyl-NH-CO-NH-CO-CHBr-CH₂Br | — | 12 |
| (32) — 2,4,5-trichlorophenyl-NH-CO-NH-CO-CHCl-CH₂Cl | 0 | 16 |
| (35) — 2,3-dimethylphenyl-NH-CO-NH-CO-CHCl-CH₂Cl | 0 | 1 |
| (34) — 2-methyl-5-chlorophenyl-NH-CO-NH-CO-CHCl-CH₂Cl | 0 | 1 |
| (36) — 3-methyl-5-chlorophenyl-NH-CO-NH-CO-CHCl-CH₂Cl | 2 | — |

Table 2-continued

*Fusicladium* test (apple)/protective

| Active compound | Infection in % at an active compound concentration of | |
|---|---|---|
| | 0.01% | 0.0025% |
| 3-CH₃, 4-Cl-C₆H₃-NH-CO-NH-CO-CHCl-CH₂Cl (37) | 0 | — |
| C₆H₅-NH-CO-NH-CO-CHBr-CH₂Br (1) | 0 | 17 |
| 4-Cl-C₆H₄-NH-CO-NH-CO-CHBr-CH₂Br (9) | — | 21 |
| 2,6-di-C₃H₇-C₆H₃-NH-CO-NH-CO-CHBr-CH₂Br (42) | | 11 |
| 2-C₂H₅, 5-C₂H₅-C₆H₃-NH-CO-NH-CO-CHCl-CH₂Cl (49) | | 2 |
| 2-C₂H₅, 5-C₂H₅-C₆H₃-NH-CO-NH-CO-CHBr-CH₂Br (50) | | 4 |
| 2-CH₃, 5-CH₃-C₆H₃-NH-CO-NH-CO-CHBr-CH₂Br (52) | | 2 |
| 2-t-C₄H₉, 5-CH₃-C₆H₃-NH-CO-NH-CO-CHCl-CH₂Cl (55) | | 0 |
| 2-C₂H₅, 5-CH₃-C₆H₃-NH-CO-NH-CO-CHCl-CH₂Cl (56) | | 0 |
| 2-CH₃, 5-(CH₃)₃C-C₆H₃-NH-CO-NH-CO-CHCl-CH₂Cl (57) | | 2 |

EXAMPLE 3

Phytophthora test (tomatoes)/protective
Solvent: 4.7 parts by weight of acetone
Emulsifier: 0.3 part by weight of alkylaryl polyglycol ether
Water: 95.0 parts by weight The amount of the active compound required for the desired concentration of the active compound in the spray liquid was mixed with the stated amount of solvent and the concentrate was diluted with the stated amount of water which contained the stated additions.

Young tomato plants with 2 to 4 foliage leaves were sprayed with the spray liquid until dripping wet. The plants remained in a greenhouse for 24 hours at 20° C and at a relative atmospheric humidity of 70%. The tomato plants were then inoculated with an aqueous spore suspension of *Phytophthora infestans*. The plants were brought into a moist chamber with an atmospheric humidity of 100% and a temperature of 18-20° C.

After 5 days the infection of the tomato plants was determined. The assessment data were converted to percent infection: 0% means no infection; 100% means that the plants were totally infected.

The active compound, the concentrations of the active compound and the results can be seen from the following table:

Table 3

*Phytophthora* test (tomatoes)/protective

| Active compound | Infection in % at an active compound concentration of 0.0031% |
|---|---|
| (known) (A) — ethylene bis(dithiocarbamate) Zn | 37 |
| (6) 3,5-dichlorophenyl-NH-CO-NH-CO-CHBr-CH₂Br | 26 |
| (7) 3,4,5-trimethoxyphenyl-NH-CO-NH-CO-CHBr-CH₂Br | 11 |
| (2) 3,4-dichlorophenyl-NH-CO-NH-CO-CHCl-CH₂Cl | 20 |
| (1) phenyl-NH-CO-NH-CO-CHBr-CH₂Br | 12 |
| (9) 4-Cl-phenyl-NH-CO-NH-CO-CHBr-CH₂Br | 5 |
| (18) 2,4-dichlorophenyl-NH-CO-NH-CO-CHCl-CH₂Cl | 30 |
| (30) 2,5-dichlorophenyl-NH-CO-NH-CO-CHCl-CH₂Cl | 35 |
| (23) 3-Cl-4-Br-phenyl-NH-CO-NH-CO-CHBr-CH₂Br | 1 |
| (33) 3-Cl-4-Br-phenyl-NH-CO-NH-CO-CHCl-CH₂Cl | 5 |
| (35) 2,4-dimethylphenyl-NH-CO-NH-CO-CHBr-CH₂Br | 5 |
| (34) 2-CH₃-4-Cl-phenyl-NH-CO-NH-CO-CHCl-CH₂Cl | 5 |
| (29) N,N-diphenyl-N'-CO-NH-CO-CHCl-CH₂Cl | 16 |
| (37) 3-CH₃-4-Cl-phenyl-NH-CO-NH-CO-CHCl-CH₂Cl | 24 |
| (24) 3,5-bis(CF₃)-phenyl-NH-CO-NH-CO-CHBr-CH₂Br | 0 |
| (38) 3,5-bis(CF₃)-phenyl-NH-CO-NH-CO-CHCl-CH₂Cl | 0 |
| (8) 2-OH-phenyl-NH-CO-NH-CO-CHBr-CH₂Br | 22 |
| (20) 3,4-dichlorophenyl-N(CH₃)-CO-NH-CO-CHBr-CH₂Br | 2 |
| (52) 2,4-dimethylphenyl-NH-CO-NH-CO-CHBr-CH₂Br | 24 |
| (56) 2-C₂H₅-4-CH₃-phenyl-NH-CO-NH-CO-CHCl-CH₂Cl | 27 |
| (60) 3,5-dimethylphenyl-NH-CO-NH-CO-CHCl-CH₂Cl | 20 |
| (62) 3,4-dimethylphenyl-NH-CO-NH-CO-CHBr-CH₂Br | 21 |
| (63) 3,5-dimethylphenyl-NH-CO-NH-CO-CHBr-CH₂Br | 17 |
| (90) 3-OCH₃-4-CH₃-phenyl-NH-CO-NH-CO-CHBr-CH₂Br | 26 |
| (91) 2-CH₃-4-OCH₃-phenyl-NH-CO-NH-CO-CHCl-CH₂Cl | 12 |

EXAMPLE 4:

Shoot treatment test/cereal rust/protective (leaf-destructive mycosis)

To produce a suitable preparation of active compound, 0.25 parts by weight of active compound was taken up in 25 parts by weight of dimethylformamide and 0.06 part by weight of alkylaryl polyglycol ether emulsifier, and then 975 parts by weight of water were added. The concentrate was diluted with water to the desired final concentration of the spray liquor.

To test the protective activity, one-leaved young wheat plants of the Michigan Amber variety were inoculated with a uredospore suspension of *Puccinia recondita* in 0.1% strength aqueous agar. After the spore suspension had dried on, the wheat plants were sprayed with the preparation of active compound until dew-moist and were placed, for incubation, in a greenhouse for 24 hours at about 20° C and 100% relative atmospheric humidity.

After 10 days' dwell time of the plants at a temperature of 20° C and 80–90% atmospheric humidity, the occurrence of rust pustules on the plants was evaluated. The degree of infection was expressed as a percentage of the infection of the untreated control plants. 0% denotes no infection and 100% denotes the same degree of infection as in the case of the untreated control. The active compound is the more active, the lower is the degree of rust infection.

The active compounds, active compound concentrations in the spray liquor and degrees of infection can be seen from the table which follows:

stir the reaction mixture, and thereafter the latter was heated to the boil and kept at the boil under reflux until the evolution of gas had ceased. The reaction mixture was then subjected to fractional distillation; this gave 220 g (61% of theory) of 2,3-dibromopropionyl isocyanate of boiling point 73° to 75° C/2.5 mm Hg.

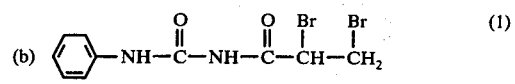

A solution of 51 g (0.2 mole) of 2,3-dibromopropionyl isocyanate in 200 ml of benzene was added dropwise in the course of 15 to 30 minutes, while stirring at 0° to 5° C, to a solution of 18.6 g (0.2 mole) of aniline in 200 ml of benzene; the mixture was then stirred for a further 15 minutes, approximately an equal volume of petroleum ether was added and the reaction product which had precipitated was filtered off and washed with petroleum ether. This gave 63 g of N-phenyl-N'-(2,3-dibromopropionyl)-urea of melting point 160° to 161° C. The yield was 90% of theory.

EXAMPLE 6

(a) Preparation of the starting material:

99 g (1.40 moles) of chlorine were passed into a solution of 100 g (1.41 moles) of acrylamide in 1,000 ml of chloroform while stirring at about 0° to 5° C. The mixture was then stirred for a further 3 hours at about 20° C, after which 270 g (2.13 moles) of oxalyl chloride was added dropwise, while continuing the stirring. The solution was then heated to the boil under reflux, until the evolution of gas had ceased. Fractional distillation of the reaction solution gave 172 g (72% theory) of 2,3-dichloro-propionyl isocyanate of boiling point 38 to 41° C/1.0 mm Hg.

Table 4

| Active compounds | Shoot treatment test / cereal rust / protective Active compound concentration in the spray liquor in % by weight | Infection in % of the untreated control |
|---|---|---|
| untreated | — | 100 |
| CH₂—NH—C(=S)—S\Zn/S—C(=S)—NH—CH₂ (known) (A) | 0.025 | 93.4 |
| (OH)C₆H₄—NH—C(O)—NH—C(O)—CHBr—CH₂Br (8) | 0.025 | 33.8 |
| (CH₃)₂C₆H₃—NH—C(O)—NH—C(O)—CHCl—CH₂Cl (35) | 0.025 | 41.3 |
| Cl₂C₆H₃—NH—C(O)—NH—C(O)—CHCl—CH₂Cl (30) | 0.025 | 33.8 |

The process of the present invention is illustrated by the following preparative Examples.

EXAMPLE 5

(a) Preparation of the starting material:

100 g (1.41 moles) of acrylamide were dissolved in 1,200 ml of chloroform and 224 g (1.41 moles) of bromine, dissolved in 250 ml of chloroform, were added dropwise to the solution at a temperature of 0° to 5° C, while stirring. The resulting suspension was stirred for a further 5 hours at 20° C. 270 g (2.13 moles) of oxalyl chloride were then added dropwise while continuing to

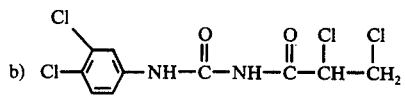
(2)

A solution of 17.0 g (0.1 mole) of 2,3-dichloropropionyl isocyanate in 50 ml of wash benzine was added dropwise to a solution of 16.0 g (0.1 mole) of 3,4-dichloroaniline in 150 ml of dry benzene at 0° to 5° C, while cooling. In the course thereof, the reaction product crystallized out. The mixture was stirred for a further hour at 20° C and was filtered, and the product was washed with petroleum ether and dried. 25 g of N-(3,4-dichlorophenyl)-N'-(2,3-dichloropropionyl)-urea of melting point 145° to 148° C, with decomposition, were obtained. The yield was 76% of theory.

EXAMPLE 7

(a) Preparation of the starting material:

A solution of 189 g (1.18 moles) of bromine in 200 ml of chloroform was added dropwise to a solution of 100g (1.17 moles) of methacrylamide in 100 ml of chloroform at a temperature of about 0° to 5° C, while stirring. The reaction mixture was stirred for a further 3 hours at about 20° C and 228 g (1.8 moles) of oxalyl chloride were then added dropwise. Thereafter the mixture was heated to the boil, under reflux, until the evolution of gas had ceased. Fractional distillation of the reaction mixture gave 248 g of 2,3-dibromo-2-methyl-propionyl isocyanate of boiling point 66° to 70° C/2.5 mm Hg. The yield was 65% of theory.

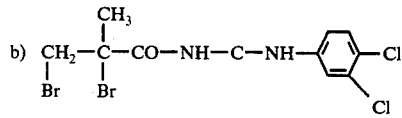
(3)

A solution of 27.0 g (0.1 mole) of 2,3-dibromo-2-methyl-propionyl isocyanate in 50 ml of wash benzine was added dropwise to a solution of 16.0 g (0.1 mole) of 3,4-dichloroaniline in 250 ml of dry benzene at 10° C. Thereupon, the reaction product crystallized out. The mixture was stirred for a further hour at 20° C and was then diluted with an equal volume of petroleum ether and filtered, and the product was dried. The yield was 39 g of N-(3,4-dichlorophenyl)-N'-(2,3-dibromo-2-methyl-propionyl)-urea (90% of theory) of melting point 202 to 204° C.

EXAMPLE 8

(a) Preparation of the starting material:

288 g (1.80 moles) of bromine were slowly added dropwise, while stirring, to a solution of 150 g (1.75 moles) of crotonic acid amide in 700 ml of dry chloroform at a temperature between −10° and 0° C. The mixture was then stirred for 3 hours at 20° C, after which 355 g (2.62 moles) of oxalyl chloride were added dropwise over the course of 1 hour. The reaction mixture was then heated under reflux until the evolution of gas had ceased. Fractional distillation gave 350 g (74% of theory) of 2,3-dibromobutyryl isocyanate of boiling point 60 to 65° C/0.3 mm Hg, as a mixture of the stereomeric forms.

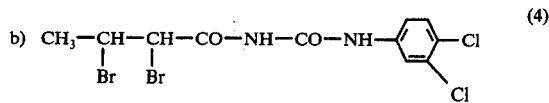
(4)

16.0 g (0.1 mole) of 3,4-dichloro-aniline were dissolved in 150 ml of dry dichloromethane and 27.0 g (0.1 mole) of 2,3 dibromo-butyrylisocyanate in 50 ml of dichloromethane were added dropwise at 0° to 5° C. The reaction product crystallized out after a short time. The batch was stirred for a further 3 hours at 20° C and was then diluted with petroleum ether and filtered, and the product was dried. The yield was 38.0 g of N-(3,4-dichlorophenyl)-N'-(2,3-dibromobutyryl)-urea of melting point 196° to 197° C, with decomposition; this represented 87% of theory.

EXAMPLE 9

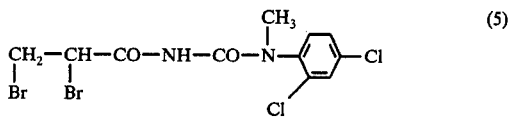
(5)

10.0 g of N-methyl-2,4-dichloro-aniline were dissolved in 150 ml of wash benzine and 15.0 g of 2,3-dibromo-propionyl isocyanate were added in separate portions at 0° to 5° C. Thereupon, the reaction product crystallized out. The mixture was stirred for a further 2 hours at 20° C and was filtered, and the product was washed with petroleum ether and dried. The yield was 22.0 g of N-methyl-N-(2,4-dichlorophenyl)-N'-(2,3-dibromopropionyl)-urea of melting point 154° to 156° C.

The following compounds of the general formula

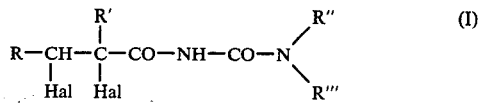
(I)

were obtained by analogous methods:

| Compound No. | Hal | R | R' | R" | R'" | Melting point (° C) |
|---|---|---|---|---|---|---|
| 6 | Br | H | H | ![3,4-dichlorophenyl] | H | 187–189 (decomposition) |

-continued

| Compound No. | Hal | R | R' | R'' | R''' | Melting point (° C) |
|---|---|---|---|---|---|---|
| 7 | Br | H | H | 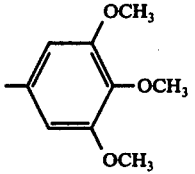 2,3,4-trimethoxyphenyl | H | 184–185 (decomposition) |
| 8 | Br | H | H | 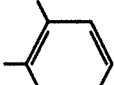 2-hydroxyphenyl | H | 163–164 (decomposition) |
| 9 | Br | H | H | 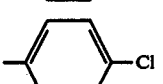 4-chlorophenyl | H | 162–163 (decomposition) |
| 10 | Br | H | H | 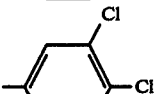 3,4-dichlorophenyl | H | 174–175 |
| 11 | Br | H | H |  naphthyl | H | 194–195 (decomposition) |
| 12 | Br | H | H | 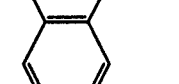 4-nitrophenyl | H | 202–204 (decomposition) |
| 13 | Br | H | H | 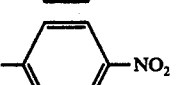 4-ethoxyphenyl | H | 172–174 |
| 14 | Br | H | H | 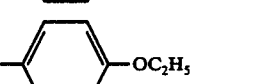 4-(phenylamino)phenyl | H | 138–142 |
| 15 | Br | H | H | 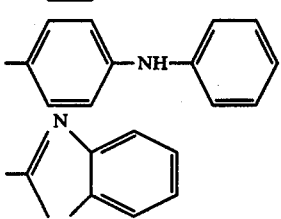 benzothiazolyl | H | 216–218 |
| 16 | Br | H | H | 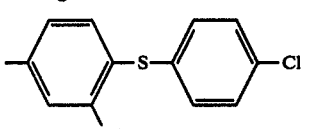 | H | 150–151 |
| 17 | Br | H | H | 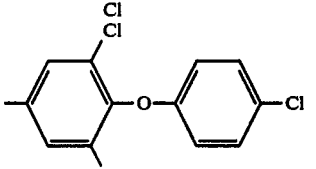 | H | 202–204 (decomposition) |
| 18 | Cl | H | H | 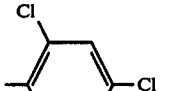 2,4-dichlorophenyl | H | 174–176 |
| 19 | Br | H | CH₃ | 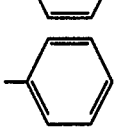 phenyl | H | 129–132 |

-continued
| Compound No. | Hal | R | R' | R'' | R''' | Melting point (° C) |
|---|---|---|---|---|---|---|
| 20 | Br | H | H | 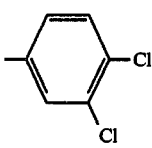 | CH$_3$ | 140–145 (decomposition) |
| 21 | Br | H | H | 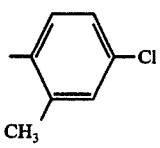 | CH$_3$ | 108–110 |
| 22 | Br | H | H | 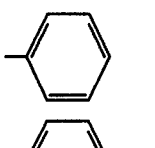 | 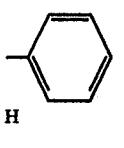 | 114–117 |
| 23 | Br | H | H | 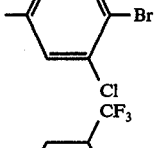 | H | 180–182 (decomposition) |
| 24 | Br | H | H | 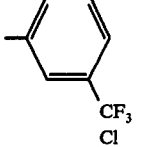 | H | 174–176 |
| 25 | Br | H | H | 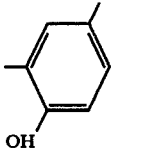 | H | 188–190 (decomposition) |
| 26 | Cl | H | H | 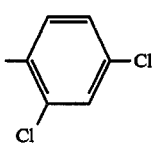 | CH$_3$ | 124–125 (decomposition) |
| 27 | Cl | H | H | 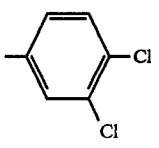 | CH$_3$ | 140–143 (decomposition) |
| 28 | Cl | H | H | 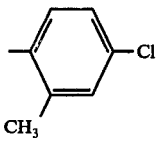 | CH$_3$ | 94–96 |
| 29 | Cl | H | H | 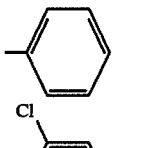 | 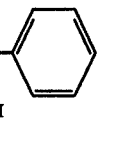 | 115–117 (decomposition) |
| 30 | Cl | H | H | 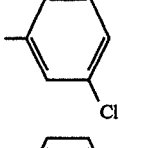 | H | 176 |
| 31 | Cl | H | H | 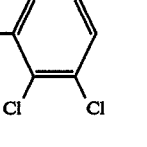 | H | 195–196 |

-continued

| Compound No. | Hal | R | R' | R" | R'" | Melting point (° C) |
|---|---|---|---|---|---|---|
| 32 | Cl | H | H | 2,4,5-trichlorophenyl | H | 180–182 |
| 33 | Cl | H | H | 4-bromo-2-chlorophenyl | H | 169–170 (decomposition) |
| 34 | Cl | H | H | 4-chloro-2-methylphenyl | H | 147–149 |
| 35 | Cl | H | H | 2,4-dimethylphenyl | H | 111–113 |
| 36 | Cl | H | H | 3-chloro-2-methylphenyl | H | 130–131 |
| 37 | Cl | H | H | 2-chloro-3-methylphenyl | H | 152–153 |
| 38 | Cl | H | H | 2,4-bis(trifluoromethyl)phenyl | H | 174–176 |
| 39 | Cl | H | H | 4-chloro-2-hydroxyphenyl | H | 177–179 |

The following compound was similarly prepared from 1,4-diamino-benzene:

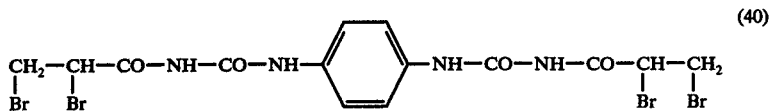

(40)

Melting point 247°–248° C (decomposition)

Further, the following compounds of the general formula (I) have been prepared by a similar process:

| Compound No. | Hal | H | R' | R" | R'" | melting point (° C) |
|---|---|---|---|---|---|---|
| 41 | Cl | H | H | $C_3H_7$-i  $C_3H_7$-i | H | 200 (decomp.) |

-continued

| Compound No. | Hal | H | R' | R'' | R''' | melting point (°C) |
|---|---|---|---|---|---|---|
| 42 | Br | H | H |  (3,5-di-i-C3H7-phenyl) | H | 206–208 (decomp.) |
| 43 | Cl | H | H | 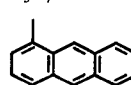 (1-anthryl) | H | 193–194 (decomp.) |
| 44 | Br | H | H | 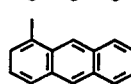 (1-anthryl) | H | 202–204 (decomp.) |
| 45 | Cl | H | H | 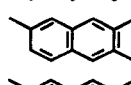 (2-anthryl) | H | 201 (decomp.) |
| 46 | Br | H | H | 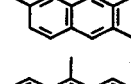 (2-anthryl) | H | 206 (decomp.) |
| 47 | Cl | H | H | 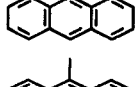 (9-anthryl) | H | 201 (decomp.) |
| 48 | Br | H | H | 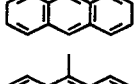 (9-anthryl) | H | 200 (decomp.) |
| 48 | Br | H | H | 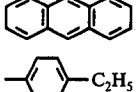 (9-anthryl) | H | 200 (decomp.) |
| 49 | Cl | H | H | 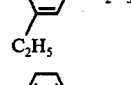 (3,4-di-C2H5-phenyl) | H | 116–117 |
| 50 | Br | H | H | 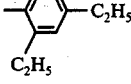 (3,4-di-C2H5-phenyl) | H | 147–149 (decomp.) |
| 51 | Cl | H | H | 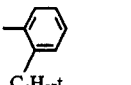 (4-t-C4H9-phenyl) | H | 141–143 (decomp.) |
| 52 | Br | H | H | 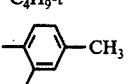 (3,4-di-CH3-phenyl) | H | 148–150 (decomp.) |
| 53 | Br | H | H | 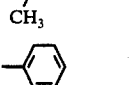 (4-t-C4H9-phenyl) | H | 166–167 (decomp.) |
| 54 | Cl | H | H | 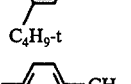 (3-i-C3H7-4-CH3-phenyl) | H | 147–150 (decomp.) |
| 55 | Cl | H | H | 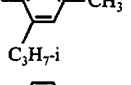 (4-t-C4H9-3-CH3-phenyl) | H | 133–134 |
| 56 | Cl | H | H | 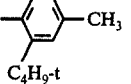 (3-C2H5-4-CH3-phenyl) | H | 119–121 |
| 57 | Cl | H | H | 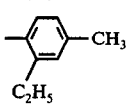 (3-CH3-4-t-C4H9-phenyl) | H | 172–174 |
| 58 | Cl | H | H | 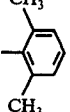 (2,4-di-CH3-phenyl) | H | 119–122 |
| 59 | Cl | H | H |  (2,6-di-CH3-phenyl) | H | 173 (decomp.) |
| 60 | Cl | H | H |  (3,5-di-CH3-phenyl) | H | 124–128 |
| 61 | Cl | H | H |  (2,4,6-tri-CH3-phenyl) | H | 165–167 (decomp.) |
| 62 | Br | H | H |  (2,4-di-CH3-phenyl) | H | 144–146 |
| 63 | Br | H | H |  (3,5-di-CH3-phenyl) | H | 163–165 |
| 64 | Br | H | H |  (2,6-di-CH3-phenyl) | H | 202 |
| 65 | Br | H | H |  (2,4,6-tri-CH3-phenyl) | H | 202 |
| 66 | Cl | H | H |  (3,4-di-t-C4H9-phenyl) | H | 145–147 |
| 67 | Cl | H | H |  (2,6-di-C2H5-3,5-di-CH3-phenyl, tetra-substituted) | H | 188 (decomp.) |
| 68 | Cl | H | H |  (phenyl) | C4H9-t | 94–97 |
| 69 | Cl | H | H |  (3,5-di-C2H5-4-CH3-phenyl) | H | 164–166 (decomp.) |
| 70 | Br | H | H |  (tetrasubstituted) | H | 197–200 |
| 71 | Br | H | H |  (3-i-C3H7-5-CH3-phenyl) | H | 159–161 |
| 72 | Cl | H | H | (3-i-C3H7-5-CH3-phenyl) | H | 142–145 |

| Compound No. | Hal | H | R' | R" | R''' | melting point (° C) |
|---|---|---|---|---|---|---|
| 73 | Cl | H | H | 3,4-dimethylphenyl | H | 165–167 (decomp.) |
| 74 | Cl | H | H | 2,3-dimethylphenyl | H | 152–155 (decomp.) |
| 75 | Br | H | H | phenyl | C₄H₉-t | 116–119 |
| 76 | Br | H | H | 3,4-dimethylphenyl | H | 182–184 |
| 77 | Br | H | H | 2,3-dimethylphenyl | H | 187–189 |
| 78 | Br | H | H | 3,5-di-t-butylphenyl | H | 177–179 |
| 79 | Cl | H | H | 2,5-di-t-butylphenyl | H | 208–210 (decomp.) |
| 80 | Br | H | H | 2,5-di-t-butylphenyl | H | 222–225 |
| 81 | Cl | H | H | 3,4,5-trimethylphenyl | H | 138–141 |
| 82 | Br | H | H | 3,4,5-trimethylphenyl | H | 181–182 |
| 83 | Br | H | H | 3,5-diethyl-4-methylphenyl | H | 192–195 |
| 84 | Cl | H | H | 3,4-dimethoxyphenyl | H | 145–147 |
| 85 | Br | H | H | 3,4-dimethoxyphenyl | H | 150–152 |
| 86 | Cl | H | H | 3,5-dimethoxyphenyl | H | 140–142 |
| 87 | Br | H | H | 3,5-dimethoxyphenyl | H | 160–164 |
| 88 | Br | H | H | 3-methyl-5-methoxyphenyl | H | 127–130 |
| 89 | Cl | H | H | 3-methyl-5-methoxyphenyl | H | 133–135 |
| 90 | Br | H | H | 3-methyl-4-methoxyphenyl | H | 149–152 |
| 91 | Cl | H | H | 3-methyl-4-methoxyphenyl | H | 121–125 |

It will be appreciated that the instant specification and examples are set forth by way of illustration and not limitation, and that various modifications and changes may be made without departing from the spirit and scope of the present invention.

What we claim is:

1. An N-aryl-N'-(2,3-dihalogeno-alkanoyl)-urea selected from the group consisting of
   N-anthracen-1-yl-N'-(2,3-dichloropropionyl)-urea,
   N-anthracen-1-yl-N'-(2,3-dibromopropionyl)-urea,
   N-anthracen-2-yl-N'-(2,3-dichloropropionyl)-urea,
   N-anthracen-2-yl-N'-(2,3-dibromopropionyl)-urea,
   N-anthracen-10-yl-N'-(2,3-dichloropropionyl)-urea, and
   N-anthracen-10-yl-N'-(2,3-dibromopropionyl)-urea.

2. The compound according to claim 1, wherein such compound is N-anthracen-1-yl-N'-(2,3-dichloropropionyl)-urea.

3. The compound according to claim 1, wherein such compound is N-anthracen-1-yl-N'-(2,3-dibromopropionyl)-urea.

4. The compound according to claim 1, wherein such compound is N-anthracen-2-yl-N'-(2,3-dichloropropionyl)-urea.

5. The compound according to claim 1, wherein such compound is N-anthracen-2-yl-N'-(2,3-dibromopropionyl)-urea.

6. The compound according to claim 1, wherein such compound is N-anthracen-10-yl-N'-(2,3-dichloropropionyl)-urea.

7. The compound according to claim 1, wherein such compound is N-anthracen-10-yl-N'-(2,3-dibromopropionyl)-urea.

* * * * *